United States Patent [19]
Fuchs et al.

[11] Patent Number: 5,102,517
[45] Date of Patent: Apr. 7, 1992

[54] CAPILLARY WASH SYSTEM

[75] Inventors: Martin Fuchs, Uxbridge; Dirk T. Broeck, Medway, both of Mass.

[73] Assignee: Millipore Corporation, Bedford, Mass.

[21] Appl. No.: 528,029

[22] Filed: May 23, 1990

[51] Int. Cl.$^5$ .................. G01N 27/26; B01D 57/02
[52] U.S. Cl. ........................... 204/180.1; 204/299 R
[58] Field of Search ............. 204/180.1, 299 R, 183.3

[56] References Cited

U.S. PATENT DOCUMENTS

| | | | |
|---|---|---|---|
| 3,506,554 | 4/1970 | Broome | 204/299 R |
| 3,620,958 | 7/1971 | Dijksterhuis et al. | 204/299 R |
| 4,152,242 | 5/1979 | Makonkawkeyoon | 204/299 R |
| 4,650,588 | 11/1987 | Diebold | 210/656 |
| 4,747,919 | 3/1988 | Anderson | 204/182.3 |

FOREIGN PATENT DOCUMENTS 0093660 4/1989 Japan .

OTHER PUBLICATIONS

J. A. Lux, H. F. Yin & G. Schomburg "Construction, Evaluation, and Analytical Operation of a Modular Capillary Electrophoresis Instrument" Chromatographia, vol. 30, No. 1/2 (Jul. 1990) pp. 7-15.

*Primary Examiner*—John Niebling
*Assistant Examiner*—John S. Starsiak, Jr.
*Attorney, Agent, or Firm*—Hamilton, Brook, Smith & Reynolds

[57] ABSTRACT

A device and method for controlling capillary injection volume is disclosed. The device is a capillary surrounded at one end by an outer jacket which is filled with a wash liquid. The outer jacket and the capillary can move relative to each other along their longitudinal axes. The open end of the capillary is moved out of the wash liquid and is dipped into a liquid sample causing some of the sample to enter the capillary. As the capillary is withdrawn from the sample, the outer jacket moves to cover the capillary until the open end is completely immersed within the wash liquid, thereby preventing an unpredictable additional volume of sample from being injected into the capillary by the residual sample solution adhering to the capillary.

11 Claims, 4 Drawing Sheets

CAPILLARY WASH SYSTEM

DESCRIPTION

1. Background of the Invention

In capillary electrophoresis, introduction of the sample is generally performed by dipping one end of the capillary into the sample solution. Hydrostatic pressure or electromigration drives a portion of the sample into the capillary. When this process is complete, the capillary is withdrawn from the sample solution. Some amount of the sample solution will adhere to the outside of the capillary, forming a droplet on the capillary end. The surface tension of the liquid in this droplet will act to drive all or part of this droplet into the capillary, resulting in unpredictable injection volume. This lack of predictability reduces the reproducibility of the analysis.

2. Summary of the Invention

The present invention relates to a device and method for controlling capillary injection volume by eliminating variability due to residual sample which clings to the sides and open end of the capillary.

The device is a capillary surrounded at one end by an outer jacket or tube having a larger inner diameter than the outer diameter of the capillary. The capillary and the outer jacket are movable relative to each other along a longitudinal axis. The space between the outer wall of the capillary and the inner wall of the jacket is filled with a wash solution, generally an electrolyte. The solution is kept in place by surface tension. The jacket can be equipped with a means for attaching it to the capillary or other part of the apparatus, and/or for moving it relative to the capillary. The outer jacket is prevented from contacting the sample solution, such as by means attached to the outer jacket.

In the present method, the end of the capillary surrounded by the jacket is moved out of the jacket and is dipped into or otherwise contacted with the sample solution in such a manner that the outer jacket does not contact the sample solution. A portion of the sample enters the open end of the capillary, for example by hydrostatic pressure difference, such as siphoning or aspiration, or by electrophoretic injection (in which the sample is moved into the capillary by an electric field. This is also termed electromigration). The capillary containing the sample is removed from contact with the sample solution and the outer jacket is allowed to move toward the open end of the capillary until the open end of the capillary is covered by the jacket and is completely immersed in the solution which is contained within the jacket. This solution washes away (i.e., dilutes to a negligible concentration) the residual sample clinging to the outer wall of the capillary and the droplet which may have formed at the open end of the capillary. The capillary, sheathed in the outer jacket, is then immersed in or otherwise contacted with an electrolyte bath and a voltage is applied to the bath to commence electrophoresis.

In another embodiment of the invention, a thin, flexible electrode wire is brought out into the outer jacket, providing electrical contact to the wash solution. With this modification, the voltage may be applied as soon as the capillary tip is withdrawn into the wash solution, beginning the electrophoretic process which continues uninterrupted when the capillary and outer jacket are immersed in the electrolyte bath.

The present device and method prevents an additional, unpredictable volume of sample from being introduced into the capillary by the droplet of residual sample solution adhering to the capillary end, thereby allowing greater control of injection volumes and enhancing reproducibility.

DETAILED DESCRIPTION OF THE INVENTION

Additional, unpredictable volume introduced by a droplet of residual sample solution adhering to the capillary end degrades the reproducibility of repeated injections in capillary systems. The present device and method of using it solves the problem by washing away the residual sample adhering to the capillary immediately after the capillary end is withdrawn from the sample solution. This prevents the surface tension of the fluid in the droplet from driving additional sample solution into the capillary during the transfer of the capillary end to the electrolyte solution in which it is immersed during the separation process.

Figure 2:
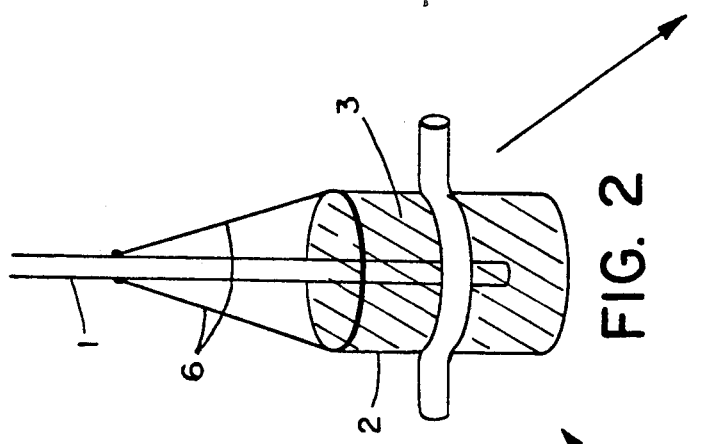
FIG. 2 is a schematic representation showing the outer jacket covering the sample-filled capillary tube.

The present device consists of a capillary and an outer jacket, which surrounds the capillary at one end, having an inner diameter larger than the outer diameter of the capillary. The outer jacket and the capillary are movable relative to each other along their longitudinal axes. The device is shown schematically in FIGS. 1, 2 and 3. As shown in FIG. 2, the outer jacket (2) is positioned relative to the capillary (1) such that the end or tip of the capillary is completely contained inside the outer jacket. For example, the outer jacket (2) can be suspended from the capillary (1) by suspending means (6). Alternatively, the outer jacket can be suspended from the device that mounts and moves the capillary (1). The suspended outer jacket (2) is sized so that the space between the inner wall of the jacket (2) and the outer wall of the capillary (1) can be filled with wash solution and remain filled while it is suspended. This can be accomplished, for example, by immersing the entire assembly (e.g., the capillary surrounded by the outer jacket) into the wash solution so that capillary action fills the space between the capillary and the outer jacket and keeps it filled. "Capillary action" in this sense means the force or action by which the surface of a liquid, is elevated (or depressed) where it contacts a solid because of the relative attraction of the molecules of the liquid for each and other and for those of the solid. A capillary tube can be generally defined as a tube having a small enough bore so that the capillary attraction of a liquid into the tube is significant.

Figure 3:
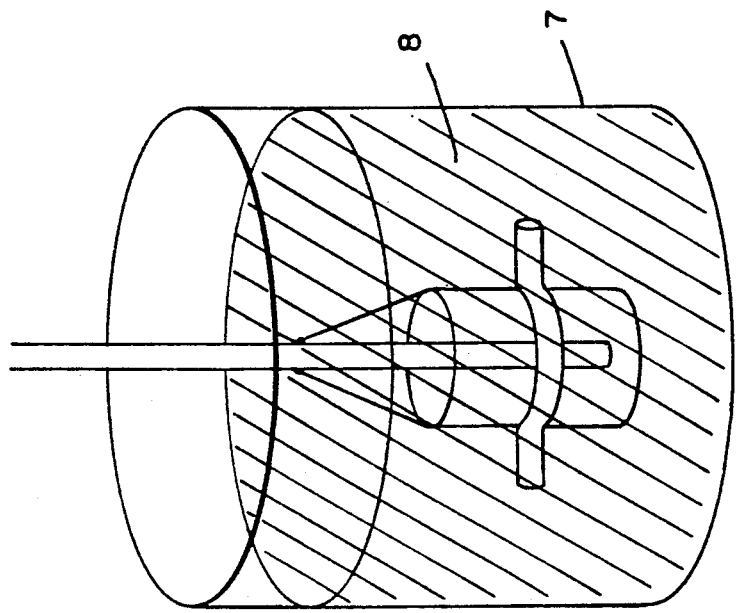
FIG. 3 is a schematic representation showing the entire assembly immersed in an electrolyte bath.
Figure 1:
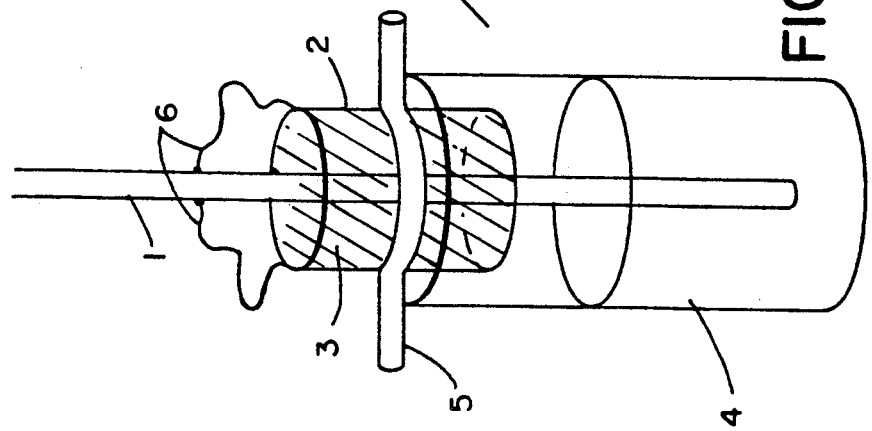
FIG. 1 is a schematic representation showing immersion of the capillary into the sample solution excluding the outer electrolyte-filled jacket.

The outer jacket preferably should not contact the sample solution during operation of the device. For this purpose, a means for preventing the outer jacket from contacting the sample can be included, if necessary to prevent the jacket from touching the sample. In one embodiment, as shown in FIGS. 1 to 3, wings (5) on the outer jacket (2) prevent it from entering the sample (4) which is generally contained in a vial or well. Thus, as the capillary (1) is lowered, only it enters the sample solution (4) during the injection process. Thereafter, as the capillary (1) is withdrawn from the sample solution (4), it moves through the wash liquid (3) in the outer jacket, so that the tip of the capillary (1) is within the liquid (3). Any residual sample solution clinging to the capillary is thereby quickly diluted into the much larger volume of fluid in the jacket (2).

The entire assembly can then be moved to and immersed in the electrolyte vessel (7) where the wash solution (3) in the jacket will equilibrate with the larger electrolyte volume (8) contained in the vessel (7). The wash solution (3) contained within the jacket (2) and the electrolyte (8) are preferably the same liquid. The separation process can then be started. For example, in capillary electrophoresis, the voltage is applied when the capillary (1) is fully immersed in the electrolyte (8). Optionally, an electrode can be placed inside the outer jacket (2), and in that case the separation could start as soon as the tip of the capillary (1) is withdrawn into the jacket (2).

The capillary used in the present device and method can be any capillary having a size and composition generally used in capillary separations, particularly in capillary electrophoresis. Such capillaries are well known in the art. For most capillary electrophoresis systems capillary tubing made of glass, teflon or fused silica having an outer diameter of from about 100 to about 600 microns is particularly useful.

The outer jacket can be composed of any material which does not chemically interact with the electrolyte or wash solution during operation of the device. The jacket material should be selected so that it is wetted by the wash solution such that it will fill by capillary action. Many types of glass, fused silica, sapphire, plastics (e.g., teflon) or metals are appropriate for this purpose. In one embodiment of the present invention, a length of glass tubing was used as the outer jacket. The size of the outer jacket should be selected so that it is capable of being substantially filled with wash solution by capillary action and will retain the wash solution when not immersed in the electrolyte. Jackets having an inner diameter of from about 300 to 3000 microns are useful for this purpose. For example, a length of glass tubing having an inner diameter of from about 700 to about 2500 microns is particularly useful for capillaries that are about 375 microns or less in outer diameter, for example. Jackets having inner diameters larger than this would work best with capillaries that have proportionally larger outer diameters.

The outer jacket is positioned relative to the capillary so that it surrounds the capillary and so that the capillary and jacket are movable relative to each other along their longitudinal axes. The outer jacket can be fastened directly to the capillary or to another part of the separation apparatus by flexible strings or other means of attachment which allows the axial movement to occur. For example, the outer jacket can be suspended from the device that mounts and moves the capillary.

During operation of the device, the space between the inner wall of the outer jacket and the outer wall of the capillary is filled with a solution which washes away the residual sample clinging to the capillary after introduction of the sample. The wash solution is selected so that it washes away (i.e., dilutes to a negligible concentration) the residual sample and does not contaminate the sample or the electrolyte when the device is immersed in the vessel of electrolyte solution for separation. Generally, the wash solution will be the same as the electrolyte.

The advantages of the present device and method are several: first, the droplet of residual sample solution on the end of the capillary is quickly washed away as the capillary is removed from the sample solution. This means that only the amount of sample introduced by hydrostatic pressure or electromigration enters the capillary. This results in much greater reproducibility and predictability of injection. Second, the outer jacket which performs the washing operation is automatically flushed with electrolyte from the larger electrolyte vessel between each sample introduction, so that multiple, reproducible injections can be performed, particularly on different samples.

The present invention is further illustrated by the following examples:

EXAMPLE 1

A capillary electrophoresis system was constructed along the lines described by Jorgenson. James W. Jorgenson and Krynn DeArman Lukacs, "Capillary Zone Electrophoresis", *Science,* 222:266–272 (1983) To the basic system he describes, in which the ends of a capillary tube are immersed in separate vessels of electrolyte each also containing an electrode for making electrical contact to the electrolyte, was added a mechanism for automating the sample introduction process. This consisted of a two-axis stepper-motor driven arm for moving one end of the capillary tube (the sample end) vertically and horizontally. The stepper-motors were controlled from a desk-top computer to move the arm. Sample introduction was accomplished by driving the arm so as to move the sample end of the capillary from one of the electrolyte containing vessels to a vessel containing sample solution. The surface of the sample solution was at a level 4.5 cm higher than the surface of the electrolyte in the vessel in which the other end of the capillary tube was immersed (the surfaces of the electrolyte in the two electrolyte reservoirs were at substantially the same levels). The immersion of the sample end of the capillary tube in the sample solution was maintained by the computer for a preselected period of time, following which the arm was driven so as to move the sample end of the capillary tube back to the initial electrolyte vessel. The transit of the capillary end from the sample solution containing vessel to the electrolyte containing vessel required approximately 27 seconds. After the sample end of the capillary tube had been reimmersed into the electrolyte, a high voltage power supply (Spellman High Voltage Electronics, Plainview, N.Y., Model RHR30PN30) connected to the electrodes (platinum wire 0.5 mm diameter, Aesar, Seabrook, N.H.) immersed in each of the electrolyte vessels was turned on to establish a longitudinal electric field in the capillary, with the sample end of the capillary being in the vessel connected to the positive terminal of the power supply. At approximately 48 cm from the sample end of the capillary, sample molecules migrating in the electric field could be detected by measuring their absorbance of a beam of ultraviolet light being passed through the capillary at this point.

A capillary tube (Polymicro Technologies, Phoenix, Ariz.) having an outer diameter of 375 microns, an inner diameter of 50 microns and a length of 60 cm was equipped on one end (the sample end) with an outer jacket of glass tubing (VWR Microdispenser Tube, VWR, San Francisco, Calif.) having a length of 13 mm and an inner diameter of 1 mm. The electrolyte vessels and the capillary tube were filled with electrolyte (0.025M $KH_2PO_4$ and 0.025M KOH). Dipping the capillary end equipped with the jacket into one electrolyte vessel caused the space between the outer jacket and the capillary to become filled with electrolyte. Attached to the outer jacket were short wings as shown in FIG. 1 that prevented the outer jacket from entering the sample solution when the arm moved the sample end over the sample vessel and pushed the tip of the capillary through electrolyte solution contained in the outer jacket into the sample solution.

Several sets of electrophoresis runs were performed with 0.5% v/v formamide in electrolyte (0.025M $KH_2PO_4$ and 0.025M KOH) as the sample solution. Under the conditions employed for these electrophoretic runs, formamide is a neutral compound, that is without a net electrical charge when in solution. Therefore its migration in the electric field in the capillary was solely due to the electrically induced flow of fluid in the capillary. This type of flow is termed electroosmosis or electroendoosmosis, and under the conditions employed for these experiments occurred from the electrolyte vessel connected to the positive terminal of the power supply to the vessel connected to the negative terminal of the power supply. Had the sample solution contained charged compounds (other than the electrolyte ions which were not detectable by the UV detector) they would have migrated faster or slower than the formamide depending on whether their charge in solution was positive or negative respectively. For these experiments, a voltage of 13 kV was used, resulting in a current of 40–42.5 microamperes.

Set out in Table 1 are the results of replicate runs of sample introduction followed by electroosmotic migration performed with and without the capillary wash system installed. The data show that significantly better results were obtained when the capillary wash system was installed.

TABLE 1

Reproducibility of Injection Volume
Relative Standard Deviation (RSD) for replicate injections

| Without Capillary Wash | With Capillary Wash |
|---|---|
| Exp. 1. RSD = 7.26%  n = 8 | RSD = 3.21%  n = 8 |
| Exp. 2. RSD = 27.60% n = 6 | RSD = 11.4%  n = 8 | n = number of samples

Figure 4:
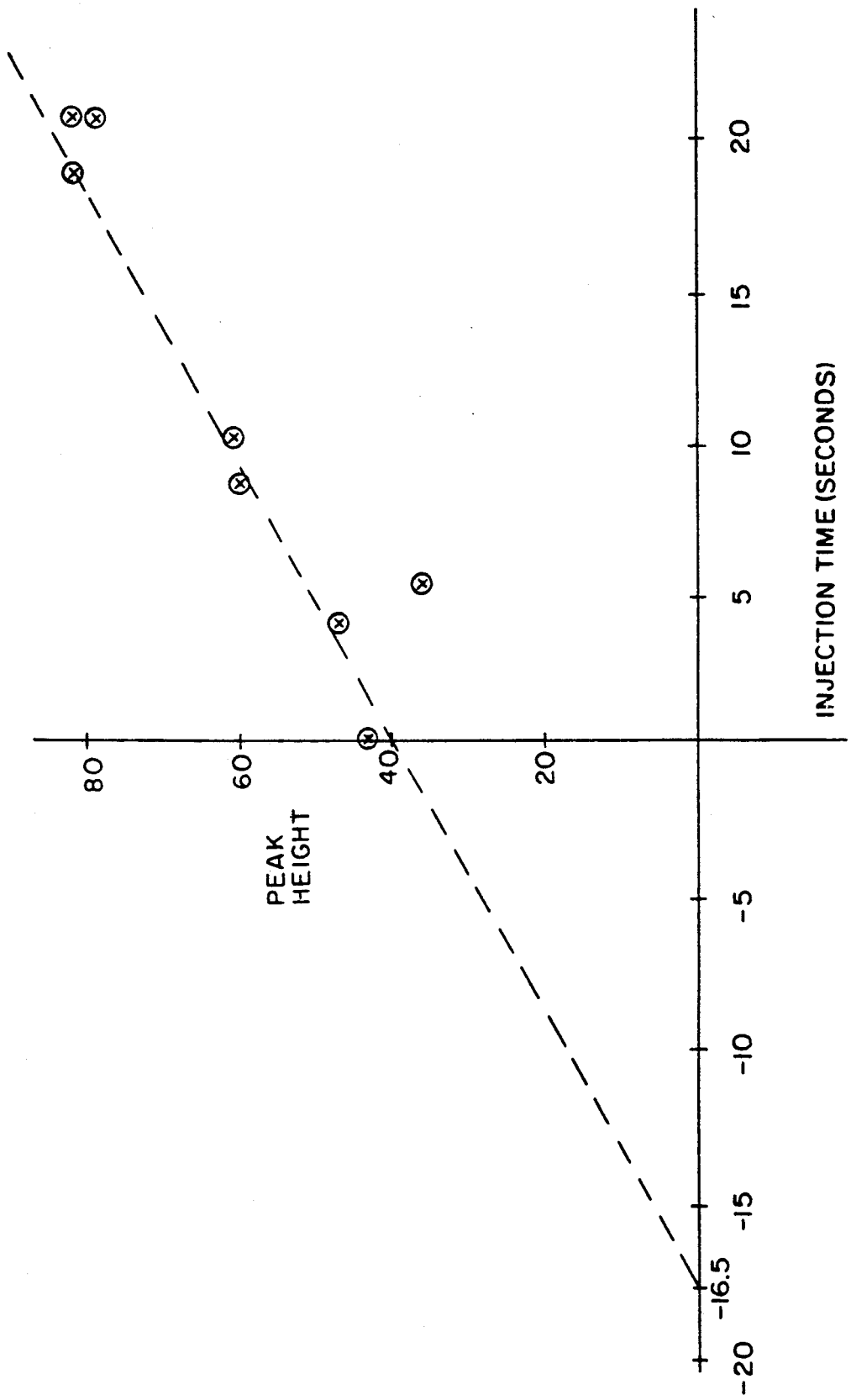
FIG. 4 is a graph plotting peak height vs. injection time without the capillary wash system. The line fitting the data points is extrapolated to zero injection time. The x-intercept approximates the amount due to residue sample.
Figure 5:
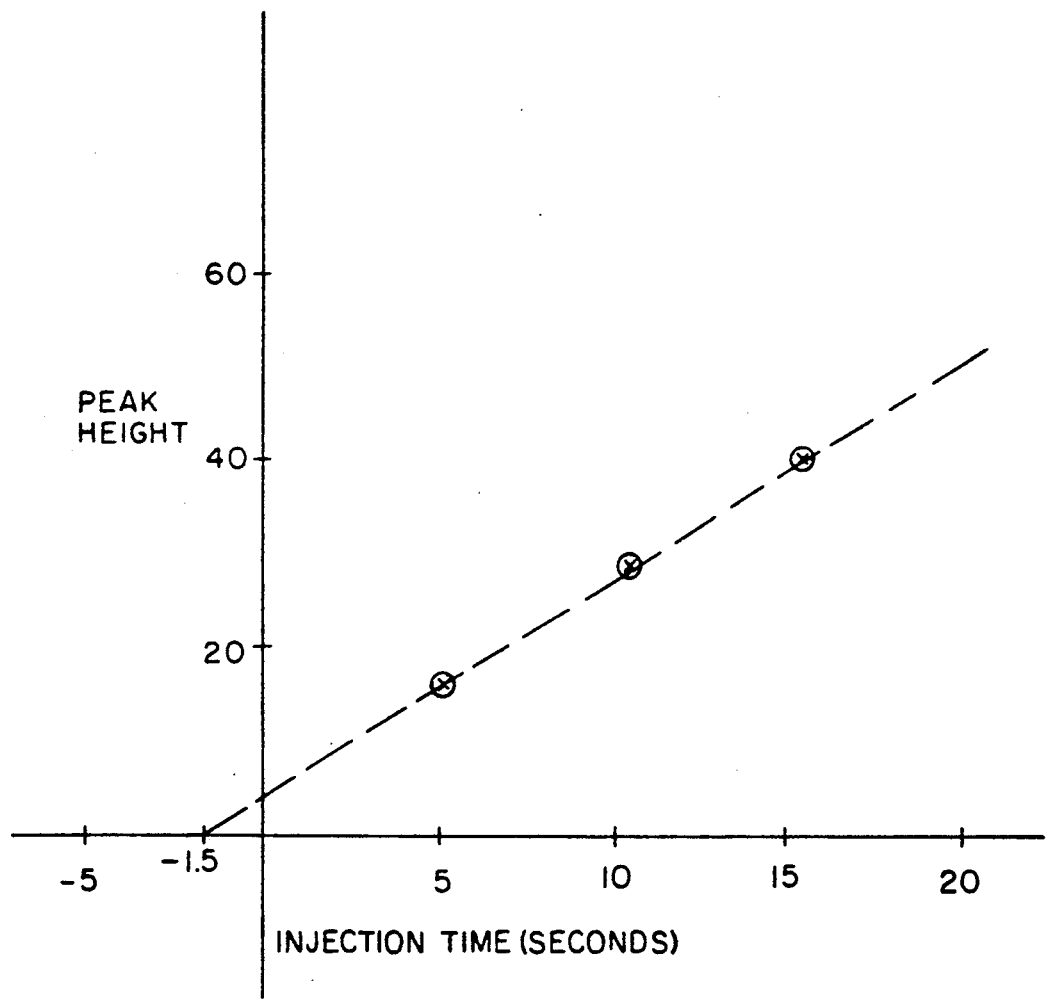
FIG. 5 is a graph plotting peak height vs. injection time for a sample tested with the capillary wash system. The line fitting the data points is extrapolated to zero injection time. The x-intercept approximates the amount due to residual sample.
Figure 6:
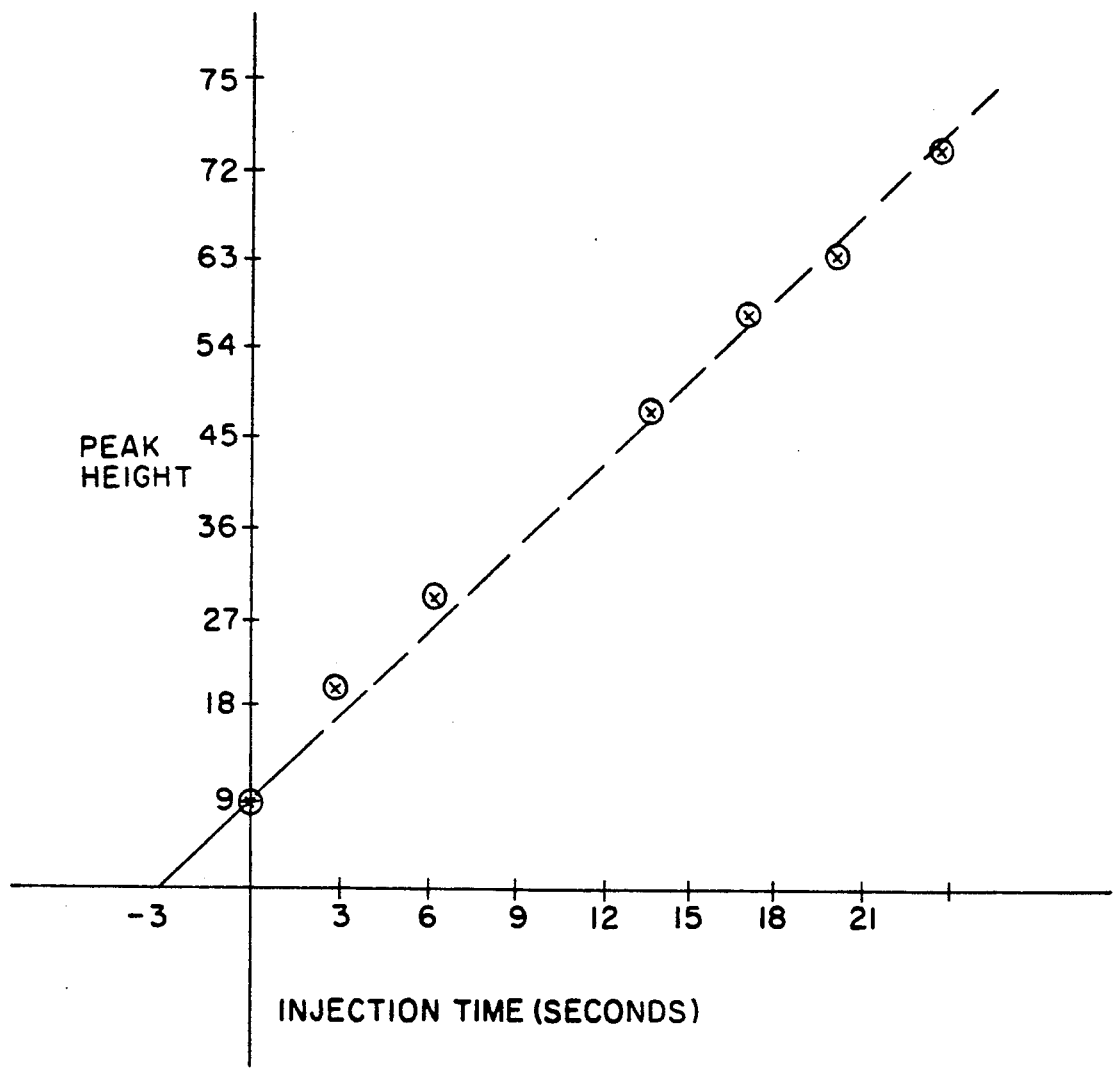
FIG. 6 is a graph plotting peak height vs. injection time. The line fitting the data points is extrapolated to zero injection time. The x-intercept approximates the amount due to residual sample.

Other results are shown graphically in FIGS. 4–6. These graphs show the amount of sample introduced as a function of injection time. Injection time is length of time the capillary was actually immersed and stationary in the sample vial and does not include the time the capillary spent travelling into and out of the sample solution, which for this system was approximately 1.5 seconds. The peak height of sample detected is proportional to the injection amount. FIG. 4 represents results obtained from injections without the capillary wash system, and FIGS. 5 and 6 are results obtained with the capillary wash system. On each of these graphs, the y-intercept is the peak height with a zero second injection time in which the capillary is moved into the sample and directly out again. The x-intercept, where the line through the data points is extrapolated to zero peak height, represents the equivalent time that would cause the "zero" time injection which approximates the amount of sample injected by the residual volume.

As shown by FIG. 4, the amount injected by a zero injection time is large, about 16.5 seconds, without the capillary wash system, equivalent to an injection time of more than 10 seconds. This is due to residual sample left on the capillary when it is withdrawn from the sample solution. In contrast, as shown by FIGS. 5 and 6, with the capillary wash system in place, the time equivalent to a zero injection is much smaller, about 1.5 to 3 seconds, equal or close to the actual time the capillary spends travelling into and out of the sample solution.

Equivalents

Those skilled in the art will recognize, or be able to ascertain, by no more than routine experimentation, many equivalents of the specific embodiments of the invention described herein. Such equivalents are intended to be encompassed in the scope of the following Claims.

We claim:

1. A device for controlling capillary injection volume comprising:

a capillary surrounded at one end by an outer jacket having a larger diameter than the capillary thereby providing a space between the inner wall of the outer jacket and the outer wall of the capillary, wherein the space between the outer jacket and the capillary contains a liquid, and wherein the outer jacket and the capillary are movable relative to each other along their longitudinal axes.

2. A device of claim 1 wherein the liquid comprises an electrolyte.

3. A device of claim 1 wherein the capillary has an outer diameter of from about 100 to about 600 microns.

4. A device of claim 1 wherein the outer jacket has an inner diameter of from about 300 to about 3000 microns.

5. A device of claim 1 wherein the capillary is composed of a material selected from the group consisting of: glass, fused silica and teflon.

6. A device of claim 1 wherein the outer jacket is composed of a material selected from the group consisting of: glass, fused silica, sapphire, plastic and metal.

7. A device of claim 1 further comprising an electrode which is positioned in the space between the inner wall of the outer jacket and the outer wall of the capillary and which is in contact with the liquid contained therein.

8. A method of controlling capillary injection volume comprising:

a. providing a capillary and an outer jacket having a larger diameter than the capillary wherein the outer jacket surrounds one end of the capillary, wherein the space between the outer jacket and the capillary is filled with a liquid, and wherein the outer jacket and the capillary are movable relative to each other along their longitudinal axes;

b. contacting the end of the capillary with a sample solution under conditions such that the outer jacket and the liquid contained therein does not contact the sample solution and a portion of the sample solution enters the capillary; and c. removing the capillary from the sample solution and allowing the outer jacket and the capillary to move longitudinally with respect to each other until the open end of the capillary is completely immersed in the liquid contained within the outer jacket.

9. A method of claim 8 wherein the outer jacket is equipped with a means for preventing it from entering the sample solution.

10. A method of claim 8 wherein the liquid contained within the space between the capillary and the outer jacket is an electrolyte.

11. A method of claim 8 wherein an electrode is positioned in the space between the outer jacket and the capillary, and contacts the liquid contained therein.

* * * * *